United States Patent [19]
Johnson

[11] 4,369,080
[45] Jan. 18, 1983

[54] MEANS FOR SENSING AND CONTROLLING THE AMOUNT OF STARCH APPLIED TO FORM CORRUGATED BOARD

[75] Inventor: Keith R. Johnson, Orland Park, Ill.

[73] Assignee: Copar Corporation, Oak Lawn, Ill.

[21] Appl. No.: 240,797

[22] Filed: Mar. 5, 1981

[51] Int. Cl.³ .......................... B05B 1/00; G01R 27/26
[52] U.S. Cl. ....................................... 156/64; 118/679; 156/356; 156/378; 324/61 R
[58] Field of Search ................. 156/356, 64, 378, 205, 156/210, 470; 118/672, 679; 425/141; 324/61 R

[56] References Cited
U.S. PATENT DOCUMENTS

| | | | |
|---|---|---|---|
| 3,222,591 | 12/1965 | Mynall | 324/61 R X |
| 3,227,951 | 1/1966 | Dykaar | 324/61 R |
| 3,378,676 | 4/1968 | Clement | 324/61 R X |
| 3,523,246 | 8/1970 | Hall et al. | 324/61 R |
| 3,584,579 | 6/1971 | Rothenberg | 324/61 R X |

*Primary Examiner*—David A. Simmons
*Attorney, Agent, or Firm*—Kinzer, Plyer, Dorn & McEachran

[57] ABSTRACT

A means for sensing the amount of a liquid bonding agent applied to secure a corrugated medium to a liner includes a capacitance device, one plate of which is formed by a sensing surface positioned adjacent the corrugated medium, liner and the applied liquid bonding agent. The other plate of the capacitance device is formed by the moving corrugated medium, liner and the applied bonding agent. There are means for applying an electric signal to the sensing surface and means for sensing variations in that signal caused by the amount of the liquid bonding agent applied to the corrugated medium and liner. The sensed variations in the applied electric signal are used to control the application of the bonding agent to the corrugated medium. The capacitance device may include a plurality of individual sensing areas having a width and spacing related to the width and spacing of the tips of the corrugated medium. The periodic signal generated by the capacitance device may be used to measure the actual amount of bonding agent, the residual moisture level in the liner and the amount of material passing from the single facer which is applying the liner to the corrugated medium.

18 Claims, 8 Drawing Figures

MEANS FOR SENSING AND CONTROLLING THE AMOUNT OF STARCH APPLIED TO FORM CORRUGATED BOARD

SUMMARY OF THE INVENTION

The present invention is directed to the field of corrugated box manufacture and has specific relation to a means for sensing the amount of liquid bonding agent, commonly referred to as starch, used in securing the corrugated medium to a liner, whether it be the single face or the double face liner. An electrical signal representative of the sensed amount of starch is then used to control the application of starch to the corrugated medium to insure a correctly bonded corrugated board.

A primary purpose of the present invention is a sensing device of the type described which uses the moving corrugated medium, liner and the starch applied thereto as one plate of a capacitance device, with an electric signal being applied to the other plate of the capacitance device which is positioned adjacent the moving liner and corrugated medium.

Another purpose is a simply constructed reliably operable capacitance sensing device useful in determining the amount of starch applied to a corrugated medium and liner.

Another purpose is a system for controlling the application of starch to a corrugated medium to insure the proper amount of starch is applied at all times.

Another purpose is a control system of the type described in which sensed variations in the application of starch to the corrugating medium are used to control the position of a doctor roll adjacent the glue or starch roll or to automatically adjust starch by the means provided thereby assuring a uniform and constant application of starch to the moving corrugated medium.

Another purpose is a sensing device of the type described which includes an electrical guard peripherally positioned about the sensing plate of the capacitance device and electrically isolated therefrom, with said guard being effective to eliminate adverse effects of stray capacitance in the circuitry associated therewith.

Another purpose is a control system of the type described using one or more such sensing devices across the width of the web to regulate the application of starch in the formation of corrugated board.

Another purpose is a capacitance device of the type described utilizing a plurality of individual sensing areas having a width and spacing corresponding to the width and spacing of the tips of the corrugated medium.

Another purpose is a control system of the type described which capacitance device will provide a periodic electric signal, with the number of periodic variations of the signal representing length of the liner and corrugated medium.

Another purpose is a control system of the type described which will provide a periodic electric signal, with the peak-to-peak variation of said signal representing the amount of liquid bonding agent applied to the corrugated medium tips.

Another purpose is a control system of the type described utilizing a capacitance device having a plurality of sensing areas corresponding to the width and spacing of the corrugated medium tips, which capacitance device will provide a periodic signal, the lower voltage of which is representative of the residual moisture in the liner.

Other purposes will appear in the ensuing specification, drawings and claims.

BRIEF DESCRIPTION OF THE DRAWINGS

The invention is illustrated diagrammatically in the following drawings wherein.

DESCRIPTION OF THE PREFERRED EMBODIMENT

Figure 1:
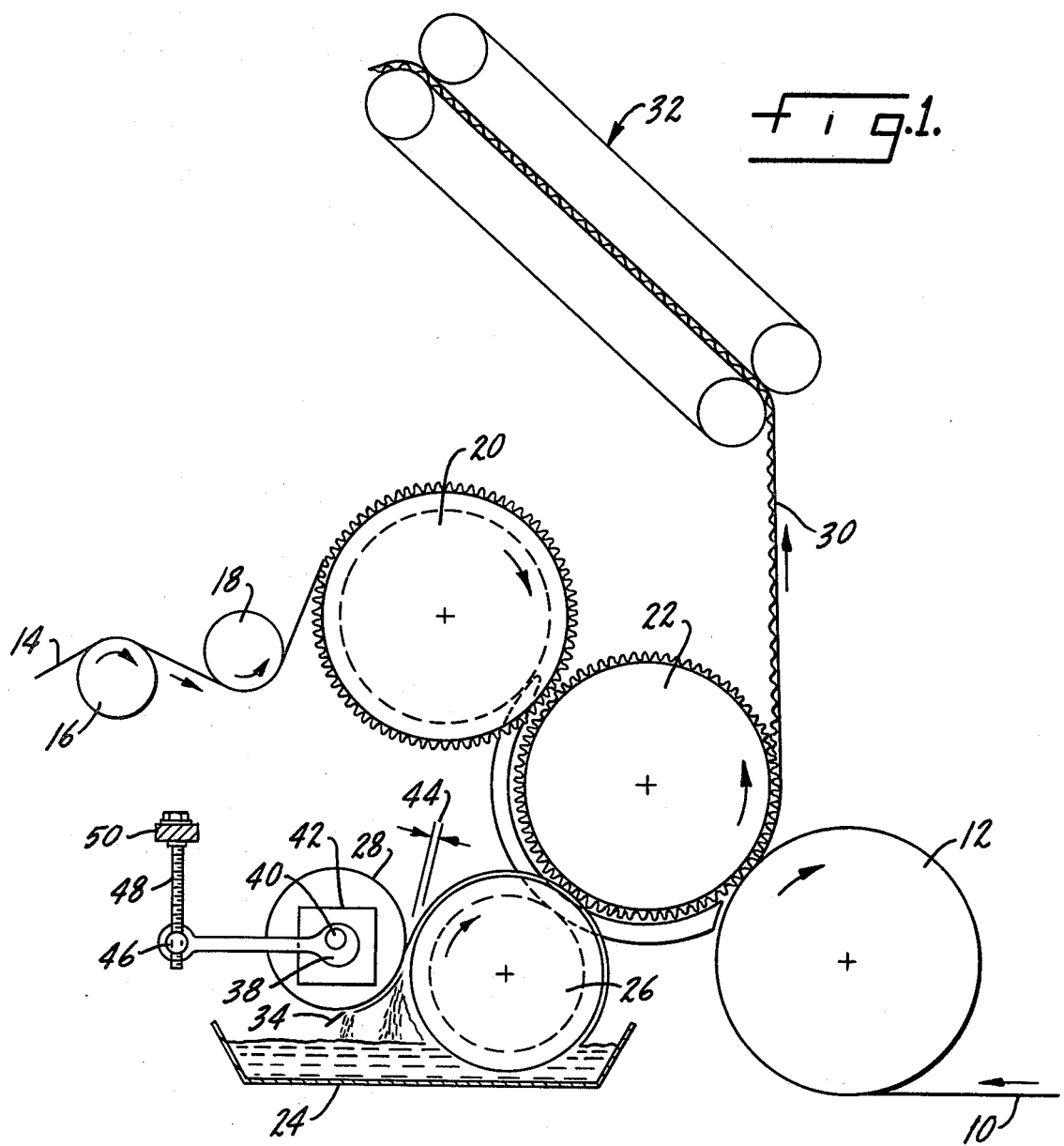
FIG. 1 is a diagrammatic showing of a portion of the machinery in a corrugating line illustrating the application of starch to a corrugated medium and the combination of a liner to said medium along with means for sensing the amount of starch and means for controlling its application.

Corrugated board is made up of three elements, a corrugated sheet which is called the medium and which is positioned between sheet material or liners. In the manufacture of corrugated board, the first operation is to join one liner to the corrugated medium as illustrated in FIG. 1. A liquid bonding agent which may be termed a glue, but which is known in the trade as starch, is applied to the tips of the corrugations, after which the liner is applied to the tips of the corrugated medium to form what is known in the art as single face material. This operation is performed in a part of the corrugator known as the single facer.

Single face material which is flexible in the machine direction, is then transported by belts to the double facer where the second liner is joined to the single face material to form corrugated board. Immediately after leaving the double facer operation, the material which is now rigid, enters the drier, after which it is split and cut into box blanks.

At both the single facer and the double facer, starch is applied to the tips of the corrugated medium by a glue roll and immediately thereafter, a liner is applied to the starched tips.

The amount of glue or starch to be applied is controlled by adjusting the clearance between the glue roll and the doctor roll. This distance may typically be adjusted manually from 0.003 inch to 0.020 inch. Unfortunately, at a fixed clearance between the glue roll and the doctor roll, the amount of starch applied to the corrugated tips per thousand square feet of either single face or double face material varies substantially with speed—sometimes as much as 3.5 to 1. Since the amount of starch applied does in fact vary considerably with speed, and since the starch contains large amounts of moisture, if the amount of starch varies with speed, thus the amount of water will also vary and the result may very well be warped board due to uneven moisture between the single face and double face liners.

The present invention is specifically directed at a means for sensing the amount of starch applied to both the single face and double face liners, or only one of such liners, and for controlling the starch application so as to overcome the problem of moisture differential caused by poorly controlled starch application between the single face and double face liners which can cause board warp. Basically the amount of moisture is sensed by a capacitive sensing device, and variations in the amount of moisture from a controlled level will initiate a change in the relative positions of a doctor roll and a glue roll, thus assuring a correct amount of starch is applied to the corrugated tips at all times.

Looking specifically at FIG. 1, a single face liner is indicated at 10 and will be applied to a corrugated medium by a pressure roll 12. The medium to be corrugated is indicated at 14 and will pass around rolls 16 and 18 to a top corrugator roll 20. Note that the surface of the roll 20 is formed in such a manner that the board passing thereover will ultimately have corrugations formed therein. A bottom corrugator roll 22 is in mesh with roll 20 and as the liner 14 passes between rolls 20 and 22 it will have corrugations formed therein.

A source of glue or starch is indicated by tank 24 and a glue roll 26 will rotate with a portion of its periphery within the tank whereby starch is applied to the exterior of the roll. A doctor roll is indicated at 28, and as will be described hereinafter, the position of the doctor roll surface relative to the surface of glue roll 26 will be adjusted to control the amount of starch actually applied to the tips of the corrugated medium.

Roll 26, as it rotates in the direction of the arrow, will apply starch to the tips of the corrugated medium which is positioned about the exterior of bottom corrugator roll 22. Shortly after the application of starch the single face liner will be applied to the corrugated medium with the result that single face material, indicated at 30, will pass upwardly from the point of pressure application of roll 12 and roll 22. Elevator belts indicated diagrammatically at 32 will convey the single face material to a further location in the corrugator where the second liner is applied. The sensing device and control of the application of starch is only shown herein in connection with the application of the single face liner to the corrugated medium. It should be understood that the same type of sensing device and control can also be used to regulate the application of the second liner to the other side of the corrugated medium. It is important that the application of starch and hence the amount of liquid applied to both sides of the corrugated medium be the same so that there is no warp of the resulting board. It is also important for purposes of economy to control the amount of applied starch.

A doctor blade 34 is positioned adjacent roll 28 to remove starch from its periphery after roll 28 has doctored starch from the surface of roll 26. The position of doctor roll 28 relative to glue roll 26 is controlled by a pair of arms, one of which is indicated at 36. Each arm 36 carries a bearing 38 which is supported in an eccentric manner in an opening 40 in a portion of the machine frame diagrammatically illustrated at 42. The adjustable clearance, indicated at 44, will vary depending upon the height of arm 36 relative to the opening 40 in the machine frame. Thus, as arm 36 is raised or lowered, in a manner to be described, this will have the effect of varying adjustable clearance 44.

Each arm 36 is mounted upon a nut 46 which is adjustable on a threaded rod 48. A portion of the machine frame is indicated at 50 and rotation of threaded rod 48, which is mounted in a non-rising manner, will cause nut 46 to move up and down on the rod thus adjusting the position of arm 36 and hence the doctor roll. There will be a similar mounting at each end of the doctor roll and once the doctor roll is arranged in strict parallelism with glue roll 26, adjustments, to be described hereinafter, will be made simultaneously to both ends of the doctor roll thus assuring that the starch is uniformly applied across the entire width of the corrugated medium.

Figure 2:
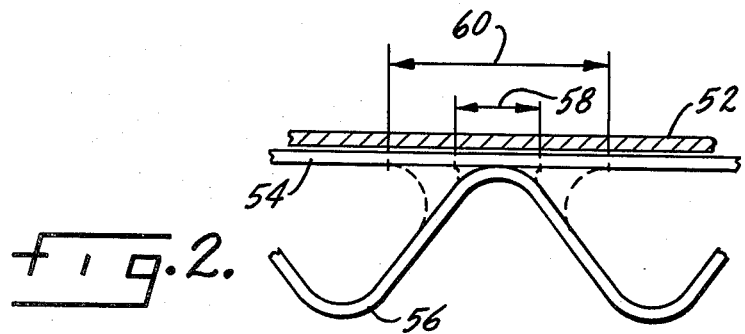
FIG. 2 is a diagrammatic illustration of the operation of a capacitance device.

FIG. 2 diagrammatically illustrates the concept of the capacitance sensor. A probe or a sensing surface is indicated at 52 and is spaced a very slight distance from or in contact with liner material 54. The corrugated medium will be formed into flutes 56 by the corrugating structure described above. The amount of starch which is applied to the tips of the corrugated medium may vary, depending upon the factors described above. Different starch application areas are illustrated by distances 58 and 60. Typically the starch will fill in the volume between the flute sides and the liner material in the manner specifically illustrated in FIG. 2. It is the application area which is to be sensed and which will be used to control the spacing between the doctor roll and the glue roll so as to provide the correct amount of starch on the corrugated tips.

Figure 3:
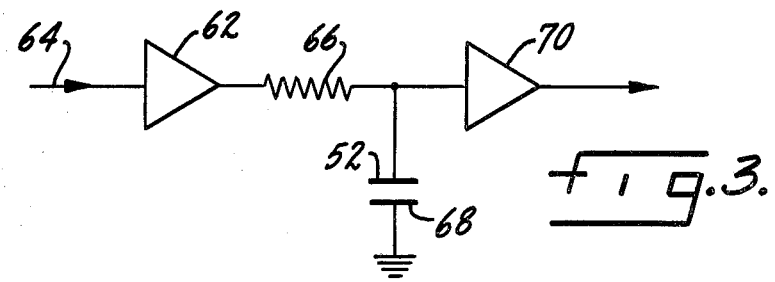
FIG. 3 is a simplified electrical diagram illustrating the operation of the capacitance device.

FIG. 3 diagrammatically illustrates the manner in which the capacitance sensing device operates. A buffer amplifier is indicated at 62 and will receive a constant frequency signal along input line 64. The output of buffer amplifier 62 is connected to a resistive element 66 which in turn is connected to sensing surface 52. The opposite plate of the capacitive device is diagrammatically illustrated at 68 and represents the starch area as defined by the liner, corrugated tips and the actual amount of starch applied, as particularly illustrated in FIG. 2. The RC circuit provides an input for a buffer amplifier 70 whose output is a signal attenuated from the input to amplifier 62 with the amount of attenuation being representative of the change in capacitance provided by the described sensing device.

A specific circuit utilizing the capacitive sensing device and providing for control of the relative positions of the doctor roll and the glue roll as described above, is illustrated in FIG. 4. The sensing device includes the described sensor plate or sensing surface 52 and the described starched area 68 as well as a peripherally positioned driven guard 72. Both the sensing plate 52 and guard 72 will receive a signal of the same potential, but these elements are electrically isolated from one another by the connection diagrammatically illustrated at 74. It is important to have a driven guard of the type described inasmuch as changes in capacitance on the order of 0.05 pf are being measured by the sensor. Stray capacitance within the described circuit elements can amount to 3.0 pf and thus it is essential that any fixed interval capacitance or extraneous surfaces be minimized or isolated and this is accomplished by maintaining the same potential at the driven guard as is on the sensor plate and by maintaining electrical isolation between these elements.

A 100 kHz oscillator 76 provides a 20 volt electric signal for the capacitance sensor. Oscillator 76 provides one input for an analog multiplier 78. The other input for multiplier 78 is provided by an error integrator indicated diagrammatically at 80. The output from multiplier 78 is connected to resistor 66. A pre-amplifier 82 is connected to a peak detector 84 as it is the peaks of the applied signal which will be detected to determine variations in capacitance. The peak detector provides one input for error integrator 80, with the other input being provided by reference voltage 86 which, for purposes of illustration, has been shown to be 2.5 volts. The analog multiplier, pre-amplifier, peak detector, and error integrator form a closed loop control. This circuit is effective to maintain a relatively constant voltage at the sensor plate of the capacitance.

Reference voltage 86 is also applied to a voltage divider network illustrated by a variable resistance 88, three series connector resistors 90, 92 and 94, and a second variable resistance 96. The error voltage from integrator 80 is connected to and forms one input for operational amplifiers indicated at 98, 100, 102 and 104, respectively. The other inputs for each of the operational amplifiers is provided by the voltage divider network. Thus, the operational amplifiers will provide output signals depending upon whether the amount of starch is at a predetermined correct level, or above or below that level. The operator may readily determine how close his machine is operating to its predetermined setting. The invention obviously should not be limited to any specific number of indicating devices or to any specific sensitivity. What is illustrated is a means for visually alerting the operator that the starch applicator is operating as required or operating at a certain degree less than required. The indicators are connected to the outputs of the operational amplifiers and are indicated at 98a, 100a, 102a, and 104a, respectively. The operational amplifier outputs are also connected to a counter/discrimination logic circuit indicated diagrammatically at 106, which logic circuit is connected to a motor 108 used to drive the threaded rod 48 illustrated in FIG. 1. Thus, the direction of drive of the threaded rod and the amount of movement of the rod will determine the tolerance or clearance between the doctor roll and glue roll which in turn will determine the amount of starch actually applied to the tips of the corrugated medium.

In summary, a capacitance sensing device is formed by a sensing plate having a predetermined voltage applied thereto. The other plate of the capacitive device is formed by the moisture area applied to the corrugated medium, with the area of the moisture being determinative of the capacitance between the two plates. The area of moisture is readily indicative of the amount of starch actually being applied and variations in the amount from a predetermined norm will cause a change in the application of starch until the predetermined norm is again reached. Thus, such variables as speed, the actual moisture content of the starch, all go into determining the actual moisture applied to the corrugating medium and the liners. As indicated above, it is important to keep the moisture content of the single face and double fact material the same. It is for this reason as well as the probable reduction in starch applied that the sensor is utilized. It is specifically the object of the sensor and the related control circuits to insure that the amount of starch applied is correct, consistent, and at the predetermined prescribed level.

Figure 4:
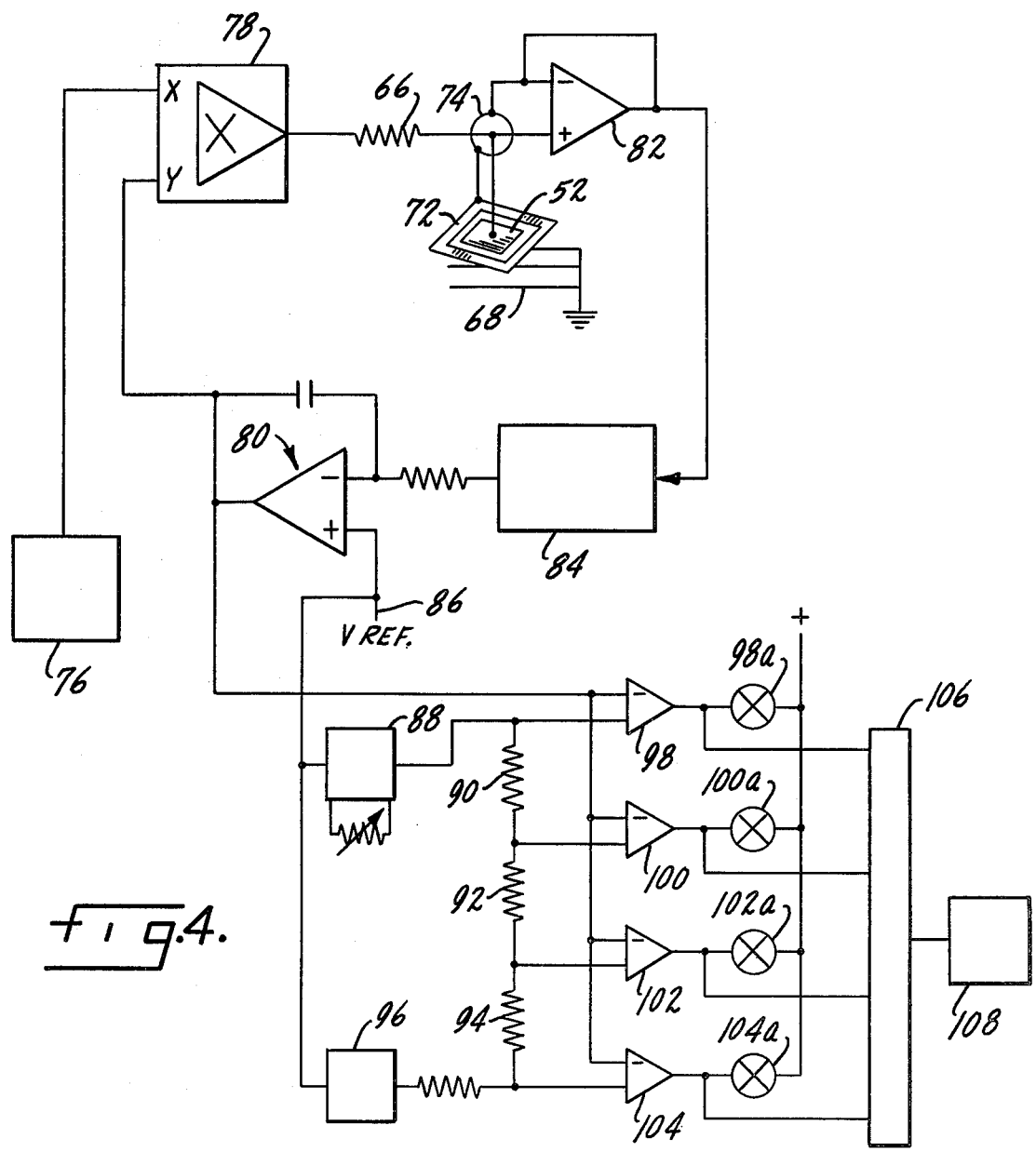
FIG. 4 is a block diagram of one suitable circuit for controlling the application of starch.
Figure 5:
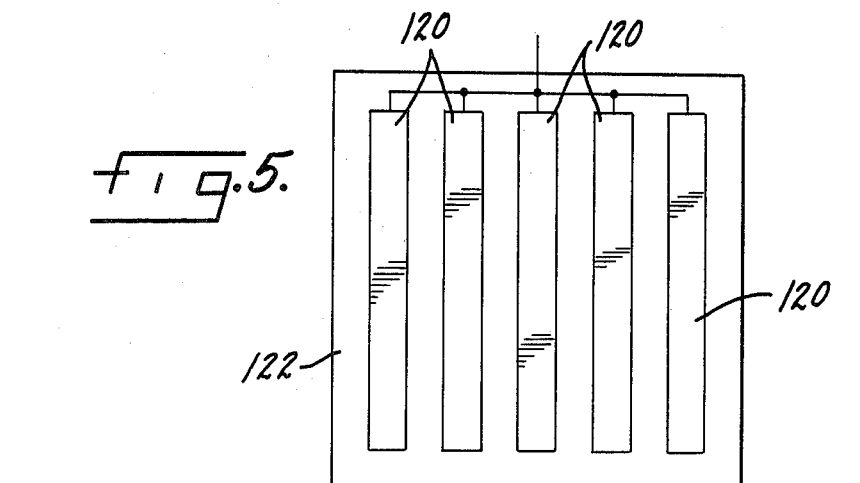
FIG. 5 is a top plan view of a variant form of capacitance device.
Figure 6:
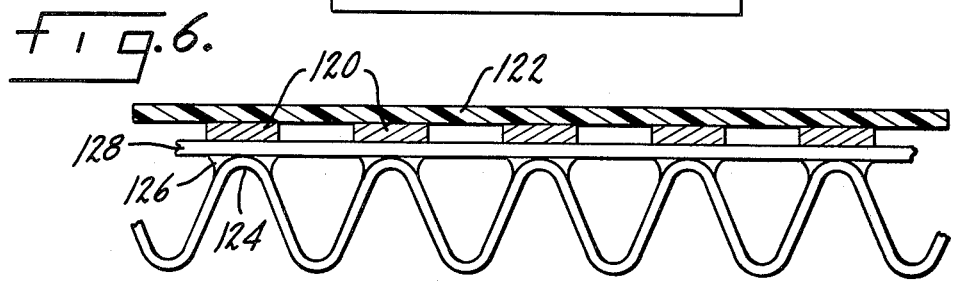
FIG. 6 is a section on an enlarged scale through a capacitance device of the type shown in FIG. 5 and positioned adjacent a corrugated medium and liner.

FIGS. 5 and 6 illustrate a variant form of capacitance sensing device. A guard such as at 72 in FIG. 4 is not shown, but one may be utilized. In this case the sensing surface or sensing area 52 of FIG. 4 has been separated into a plurality of parallel sensing areas indicated at 120. The areas 120 will be connected in parallel in terms of the applied input signal. The spacing of the parallel areas 120 will correspond to or be representative of the spacing between the tips of a typical corrugated medium. The corrugated box industry has different spacings of the flutes or tips, depending upon the type of box. For example, the spacing or pitch may be 0.187 inch, 0.93 inch or 0.140 inch. The invention obviously should not be limited to any particular spacing and the above are merely examples of commonly used spacings in the industry.

FIG. 6 diagrammatically illustrates the relationship between the parallel sensing areas 120 and the tips of the corrugated medium. The sensing areas will be applied to a support member 122 which may be typical of printed circuit board type devices and may be formed of a suitable epoxy. As illustrated in FIG. 6, the tips 124 of the corrugated medium with the associated starch areas 126 are positioned against a liner 128 and directly in alignment with the sensing areas 120. A slight movement to the right, assuming that is the direction of travel of the single face material, will cause the starch and tips to be positioned between sensing areas 120. The result of continuous movement of the single face material past the sensing areas will be an output signal from the capacitance device in the nature of a periodic wave, for example the sine wave illustrated in FIG. 8. The peak voltage of the sine wave will be produced when the starch and tips are in the position of FIG. 6 and the lowest voltage of the periodic waveform of FIG. 8 will be produced when the starch and tips are midway between sensing areas 120.

Figure 8:
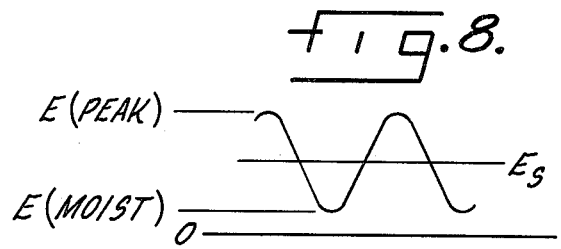
FIG. 8 is a diagrammatic illustration of the waveform provided by the capacitance device of FIGS. 5 and 6 illustrating uses for such waveform in measuring residual moisture and the amount of a liquid bonding agent.

The periodic signal of FIG. 8 has several uses. First, it can provide material measurement for the amount of material leaving the single factor. Second, it can provide an indication of the actual level of starch applied to the corrugated medium tips and, lastly, it can provide an indication of the residual moisture level in the liner material.

Figure 7:
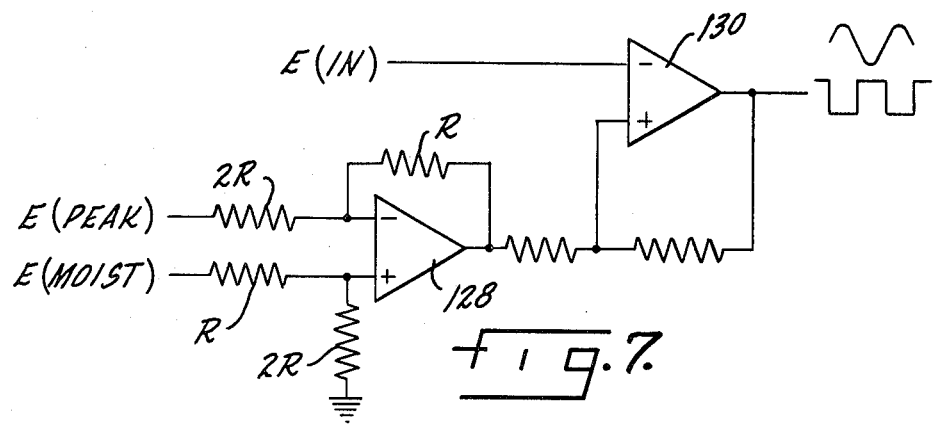
FIG. 7 is a diagrammatic illustration of a simplified electrical circuit for using the periodic waveform provided by the capacitance device of FIGS. 5 and 6.

Considering first the utility as a measurement of material leaving the single facer, which material will conventionally go to a holding area or bridge prior to the time that a second liner is applied at the double facer, FIG. 7 illustrates an electrical circuit utilizing the periodic waveform of FIG. 8 as a means of material measurement. An operational amplifier 128 has one input of the negative peak voltage from FIG. 8 and a second input of the positive lower voltage of FIG. 8. These voltages have been designated E (peak) and E (moist) in FIG. 8. A resistor 2R is connected at the E (peak) input and a resistor R is connected at the E (moist) input. Additional resistors of 2R and R are connected in circuit with the operational amplifier as is conventional in the art. The output from amplifier 128 is a DC level which is equal to the center of the AC waveform designated $E_s$. This voltage is applied to a second operational amplifier 130 at the positive input with the negative input being the signal applied to the series of sensing areas 120. The output from operational amplifier 130 will be a square wave having the frequency of FIG. 8 which square wave will be independent of the actual E (peak) and E (moist) voltage levels. Such a square wave can be used in a conventional footage counter typically used in the corrugated box industry to measure the length of material moving from one area to another. Thus, the capacitance device, which relies upon moisture as a means for generating a periodic waveform, can provide a signal which is useful in measuring the footage of material passing from the single facer to the holding area or bridge.

A second use of the periodic waveform of FIG. 8 is to provide an actual measurement of the starch applied by the applicator of FIG. 1. In this case the difference between the E (peak) and E (moist) is representative of the actual starch level. In other words, the peak-to-peak value of the periodic waveform of FIG. 8 will represent the actual level of applied starch.

Further, the level of residual moisture in the liner which is represented by E (moist) can similarly be determined. E (moist) is equal to E (peak) minus twice the value the voltage applied to the sensing area.

The electrical circuitry to provide the voltages indicative of the moisture level of the liner and the actual level of starch applied to the corrugated tips is state-of-the-art and has not been described in detail herein.

The invention should not be limited to any particular type of electronic control. What is important is the use of a capacitive device for sensing variations in moisture content with variations in capacitance reflecting changes in moisture or applied starch. The sensing device can be used in any number of ways to effect control of the amount of applied starch.

Another method of controlling the amount of starch applied to the tips of the medium corrugations is to vary the difference in peripheral speed between the glue roll and the corrugator roll. This method also utilizes a doctor roll by means of which the machine operator can vary the thickness of the layer of starch on the glue roll. Once the thickness of the layer of starch has been established, the difference in speed between the two surfaces will vary the amount of starch deposited on the corrugations by increasing or decreasing the differential speed and thereby the wiping action of the corrugations against the glue roll. The control described herein can be used to control the doctor roll/glue roll gap; the differential of the peripheral speeds or both. In either case (doctor roll/glue roll clearance or differential peripheral speed control) the sensor makes a closed loop control feasible.

Whereas the preferred form of the invention has been shown and described herein, it should be realized that there may be many modifications, substitutions and alterations thereto.

I claim:

1. A means for sensing the amount of a liquid bonding agent applied to secure a corrugated medium to a liner, including a capacitance device, one plate of which is formed by a sensing surface positioned adjacent the corrugated medium, liner and applied liquid bonding agent, the other plate of said capacitance device being formed by the corrugated medium, liner applied liquid bonding agent, means for applying an electric signal to said sensing surface, and means for sensing variations in said signal caused by the amount of said liquid bonding agent applied to said corrugated medium and liner.

2. The sensing means of claim 1 further characterized in that said sensing plate includes a guard element, electrically isolated from said sensing plate, and having the same signal applied thereto as applied to said sensing plate, thereby eliminating the effects of stray circuit capacitance on variations in said signal.

3. The sensing means of claim 2 further characterized in that said guard element is positioned peripherally about the conductive area of said sensing plate.

4. The sensing means of claim 1 further characterized by and including a resistive element in circuit with said sensing surface whereby the combination of said capacitance device and resistive element form an RC circuit.

5. Means for controlling the application of a liquid bonding agent by a rotating roll to a moving corrugated medium, which medium will be attached to a moving liner, including a capacitance device, one plate of which is formed by a sensing surface positioned adjacent the combined moving corrugated medium and liner, the other plate of said capacitance device being formed by the moving corrugated medium, liner and the applied liquid bonding agent, means for applying an electric signal to said sensing surface, means for sensing variations in said signal caused by the amount of said liquid bonding agent applied to said corrugated medium, and means for varying the application of said bonding agent by said rotating roll to the moving corrugated medium in accordance with sensed variations in said signal.

6. The controlling means of claim 5 further characterized in that said sensing plate includes a guard element, electrically isolated from said sensing plate, and having the same signal applied thereto as applied to said sensing plate, thereby eliminating the effects of stray circuit capacitance on variations in said signal.

7. The controlling means of claim 6 further characterized in that said guard element is positioned peripherally about the conductive area of said sensing plate.

8. The controlling means of claim 5 further characterized by and including a resistive element in circuit with said sensing surface whereby the combination of said capacitance device and resistive element form an RC circuit.

9. The controlling means of claim 5 further characterized in that adhesive applied by said rotating roll is determined by the spacing between that roll and an adjacent doctor roll, with said means for varying the application of adhesive varying the spacing between the doctor roll and rotating roll.

10. The controlling means of claim 5 further characterized in that adhesive applied by said rotating roll is determined by the spacing between that roll and an adjacent doctor roll, with said means for varying the application of adhesive varying the differential speed between said rotating roll and said moving corrugated medium.

11. The controlling means of claim 5 further characterized by and including a plurality of capacitance devices, all positioned adjacent the moving corrugated medium and liner, with the variations in electric signals caused by said capacitance devices controlling the means for varying the application of said liquid bonding agent by said rotating roll.

12. Sensing means for providing a periodic electric signal representative of moisture applied to the tips of a corrugated medium as part of a bonding agent to secure a liner thereto including a capacitance device, one plate of which is formed by a sensing surface positioned adjacent the corrugated medium, liner and applied bonding agent, the other plate of said capacitance device being formed by the corrugated medium, liner and applied bonding agent, said sensing surface including a plurality of individual sensing areas having a width and spacing related to the width and spacing of said tips whereby there can simultaneously be register between each of said sensing areas and a tip, means for applying an electric signal to said individual sensing areas, and means for sensing variations in said signal caused by variations in applied moisture.

13. The sensing means of claim 12 further characterized in that the number of periodic variations of said signal represent length of said liner and corrugated medium.

14. The sensing means of claim 12 further characterized in that the peak-to-peak variations of said periodic signal represent the amount of applied liquid bonding agent.

15. The sensing means of claim 12 further characterized in that the lowest voltage of said periodic signal, as compared with a reference voltage, represents the residual moisture in the liner.

16. A method of measuring the amount of liner and corrugated medium passing from a single facer including the steps of passing the single face material adjacent a capacitive sensing device responsive to moisture from the bonding agent used in securing the corrugated medium to the liner, using said capacitance device to generate a periodic electric signal, with a period of said signal representing the spacing from one tip of the corrugated medium to an adjacent tip.

17. A method of measuring the residual moisture level in the liner used in the formation of single face material consisting of a liner and a corrugated medium, directly after said liner has been secured by a liquid bonding agent to said corrugated medium including the steps of passing the single face material adjacent a capacitive sensing device responsive to moisture from the bonding agent, using said capacitance device to generate a periodic electric signal, with the residual moisture level of the liner material being represented by the lower voltage of said periodic signal.

18. A method of measuring the amount of a liquid bonding agent applied to a corrugated medium, which bonding agent is used to secure a liner to said corrugated medium, including the steps of passing the single face material consisting of the liner and corrugated medium with the liquid bonding agent applied thereto adjacent a capacitive sensing device responsive to moisture from the bonding agent, using said capacitance device to generate a periodic electric signal, with the peak-to-peak voltage of said periodic signal being representative of the amount of applied liquid bonding agent.

* * * * *